United States Patent [19]

Huang

[11] Patent Number: 5,530,245

[45] Date of Patent: Jun. 25, 1996

[54] SURFACE CHARACTERIZATION OF CATALYTIC MATERIALS BY POSITRON ANNIHILATION RADIATION LINESHAPES MEASUREMENTS

[76] Inventor: Wei-Feng Huang, 7100 Cove Pointe Pl., Prospect, Ky. 40059

[21] Appl. No.: 239,956

[22] Filed: May 9, 1994

[51] Int. Cl.$^6$ ................................... G01N 23/22
[52] U.S. Cl. ............... 250/307; 250/308; 250/363.03
[58] Field of Search .................. 250/307, 308, 250/363.03

[56] References Cited

U.S. PATENT DOCUMENTS

| | | | |
|---|---|---|---|
| 4,864,131 | 9/1989 | Rich et al. .................. | 250/308 |
| 4,897,549 | 1/1990 | Zerda et al. .................. | 250/358.1 |
| 5,015,851 | 5/1991 | Singh et al. .................. | 250/307 |
| 5,200,619 | 4/1993 | Asoka-Kumar et al. .................. | 250/308 |

*Primary Examiner*—Jack I. Berman
*Attorney, Agent, or Firm*—Scott R. Cox

[57] ABSTRACT

Positron annihilation radiation lineshapes from two-dimensional angular correlation and Doppler broadened spectrum measurements are used to monitor specific surface acidity (proton concentration per unit surface area) of catalytic materials with large internal surface areas. Annihilation gamma lineshape parameter increases with internal surface area and decreases with specific surface acidity as a result of oxidation of positronium atoms at the surface by protons. These results point to a new and effective method for specific surface acidity valuations.

3 Claims, 10 Drawing Sheets

SURFACE CHARACTERIZATION OF CATALYTIC MATERIALS BY POSITRON ANNIHILATION RADIATION LINESHAPES MEASUREMENTS

BACKGROUND OF THE INVENTION

1. Field of the Invention

This invention relates to methods for characterizing surfaces of catalytic materials by using positron annihilation radiation lineshapes. More specifically, it relates to the detection of changes in surface area, surface acidity, and specific surface acidity of zeolite catalysts by using positron annihilation radiation lineshapes produced by a single high resolution gamma detector or by two-dimensional angular correlation measurements. In this particular field of surface characterization of zeolite catalysts, the emphasis is upon extending the positron annihilation technique to the achievement of an in-situ, efficient, and non-destructive method for the measurements of surface area and acidity.

2. Background Information

Zeolite catalysts with large internal surface areas (in hundreds $m^2/gm$) play a vital role in certain sectors of the chemical industry. For example, catalysts of zeolites incorporated in silica, silica-alumina, and silica-clay materials can drastically improve the yield of petroleum-cracking process, resulting in saving the refineries billions of dollars every year. Zeolite ZSM-5, as another example, was found to be invaluable in some large-scale processes, such as M-forming (increasing octane number in gasoline), dewaxing, high yield ethylbenzene production and methanol (from coal or natural gas) conversion to high grade gasoline, etc.

The catalytic process is rather complicated. It primarily involves such factors as diffusion and adsorption of reactants on the catalyst surface, desorption and diffusion of products away from the surface, etc. It is apparent, therefore, that the size, shape, and chemical characteristics of the internal surfaces are crucially related to the activity and performance of the catalyst. In the face of increasing demand for improvements in air quality as required by the environmental regulations and improvement in fuel efficiency, the need to understand and to search better ways to characterize zeolite catalysts has become ever more urgent and important.

Conventional methods of acidity evaluation include UV-visible spectroscopy (Hammett-type measurements), study of thermal deposition of salts, measurement of heat of interaction with bases, and measurement of rates of model reactions.

The Hammett-type measurements are not useable for practical purposes, because real life catalysts are normally colored and opaque. The thermogravimetric and calorimetric techniques have not been able to distinguish the effects of protonation of the base from the effects of other types of interaction of the base with the catalyst. The method based on reaction kinetics requires an intimate knowledge of the reaction mechanism itself which is often based on postulations. Measurement of the protonation by C-13 NMR method has a low sensitivity and requires the use of concentration of base whose cancellation of the activity term is not usually available (Reference 7).

Other traditional methods for the determination of surface properties of zeolites, for example, the chemisorption method for measuring surface acidity of zeolites, often yield inconsistent results among different laboratories, and at times fail to provide a valid assessment on the activity of the zeolite.

Positron annihilation is an unconventional, in-situ microprobe for monitoring electronic properties of the sample. Its principle is based on the fact that positrons, the positively charged anti-particle of electrons, when impregnated in the sample, always annihilate with electrons in the sample material, resulting in gamma rays according to the famous energy-matter equation $E=mc^2$ which is 511 KeV for an electron. The method includes three techniques, namely, positron lifetime, angular correlation (one-, and two-dimensional), and annihilation radiation lineshape measurements. Prior art in the field almost exclusively employed positron lifetime technique for the characterization of catalytic and porous materials.

In order to provide background information so that the invention may be completely understood and appreciated in its proper context, reference is made to a number of prior publications as follows:

Reference 1, authored by J. Lahtinen and A. Vehanen, provides an overview of the positron techniques as applied to surface studies. It extensively reviewed in particular the application of positron lifetime method.

Reference 2, authored by Y. Ito and T. Takano, presented positron lifetime and one-dimensional angular correlation data for a series of synthetic zeolites. Results were correlated to the size of voids, not surface properties, of materials.

Reference 3, authored by K. Venkateswaran, K. L. Cheng, and Y. C. Jean, illustrated the application of positron lifetime technique to porous resins. A correlation between the intensity of the long-lived ortho-positronium and the effective surface area was shown.

Reference 4, authored by M. B. Perkal and W. B. walters, reported results of studies of zeolites 4A and 13X by positron technique, still by positron lifetime measurements. The results were considered to be related to pore sizes.

Reference 5, authored by H. Nakanishi and Y. Ujihira, is pertinent to showing results of application of the positron techniques to the characterization of some zeolites, primarily by positron lifetime and, to a much lesser extent, by Doppler-broadening measurements. Its purpose was to study the character of zeolite cages.

Reference 6, authored by W. F. Huang, R. Ochoa, and R. Miranda, uses Doppler broadened positron annihilation spectra in silica-alumina to demonstrate that positroniums formed in this material preferentially interact with Bronsted acid sites, not with Lewis acid sites.

Reference 7, authored by D. Farcasiu, G. Miller, A. Ghenciu, and H. S. Cao, discusses deficiencies of various conventional methods of determining the acidity of catalysts and presents a modification to the technique of C-13 NMR measurements.

Positron lifetime spectrum, as employed by previous investigators, has complex structures in molecular substances. It can have two, three, or four components which superimpose on each other, forming a continuous distribution. The number of components to be used for analysis is arbitrarily decided. And the specific lifetime component chosen to correlate with material's characteristics varies among investigators. The intensity of any particular time component often lacks the consistency that may enable interpretation of results.

Positron lifetime technique is inherently a time-inefficient method. Because of the requirement of low counting rate for positron lifetime measurement, a single lifetime spectrum usually takes several days. One-dimensional angular correlation of the annihilation radiation is also a very time consuming process due to the extremely fine opening required for the parallel slits system used in this technique. All the useful annihilation radiation outside the fine slits are not utilized. It is, therefore, neither a positron source effective, nor a cost effective technique. On the other, using the half-width of the narrow component of the one-dimensional angular correlation spectrum has not shown any correlation with the internal surface parameters.

Whatever the precise merits, features and advantages of the above cited references, none of them achieves or fulfill the purposes of surface characterization of catalytic materials by using positron annihilation radiation lineshapes in the present invention.

It is therefore the principal object of the present invention to provide an efficient, in-situ method which can directly provide information about surface characteristics of catalytic materials.

SUMMARY OF THE INVENTION

This invention comprises a process for obtaining relative values of surface area, surface acidity, and specific acidity of catalytic materials, particularly zeolites, by measuring gamma lineshapes resulted from annihilation of positrons and positronium atoms in the material.

DETAILED DESCRIPTION

1. Principles of Positron Techniques

Positrons, the anti-particle of electrons, always annihilate with electrons in the subject material, resulting mostly in two gamma rays propagating in opposite direction. Each gamma ray has a broad gaussian-shaped energy distribution curve centered at 511 KeV. Some of the positrons impregnated in the target sample will form hydrogen-like bound system with electrons. They are positronium atoms. Angular distribution of the two emerging gamma rays reveals the momentum distribution of the electrons in the sample. It also has a broad gaussian distribution.

Gammas from annihilation of positronium atoms have a much narrower energy and momentum distributions superimposing over the regular gaussian-shaped distributions and thus contributing to the intensity of the central region of total gamma distributions. Consequently, when the population of positronium changes, the overall shape of the energy and momentum distribution curves also change. Changes in the energy and momentum curves are gauged by a lineshape parameter S which is defined as the ratio of the area of the narrow central region of the distribution curves and the total area under the curves. Accordingly, when positronium population in the sample decreases, it reduces the intensity of the central region of the energy and momentum distribution curves, the lineshape parameter S will become correspondingly smaller.

In porous materials, e.g. zeolites, positroniums form only on the near surfaces, not in the crystalline bulk. The population of positronium atoms on the surfaces as well as the shapes of the distribution curves in these materials is influenced by surface characteristics such as the size of the surface area and the degree of surface acidity. This constitutes the theoretical basis of this invention which uses the lineshape parameters for the surface characterization of these materials. Details of each method and examples are described below.

2. Energy Distribution Curve Method

Figure 1:
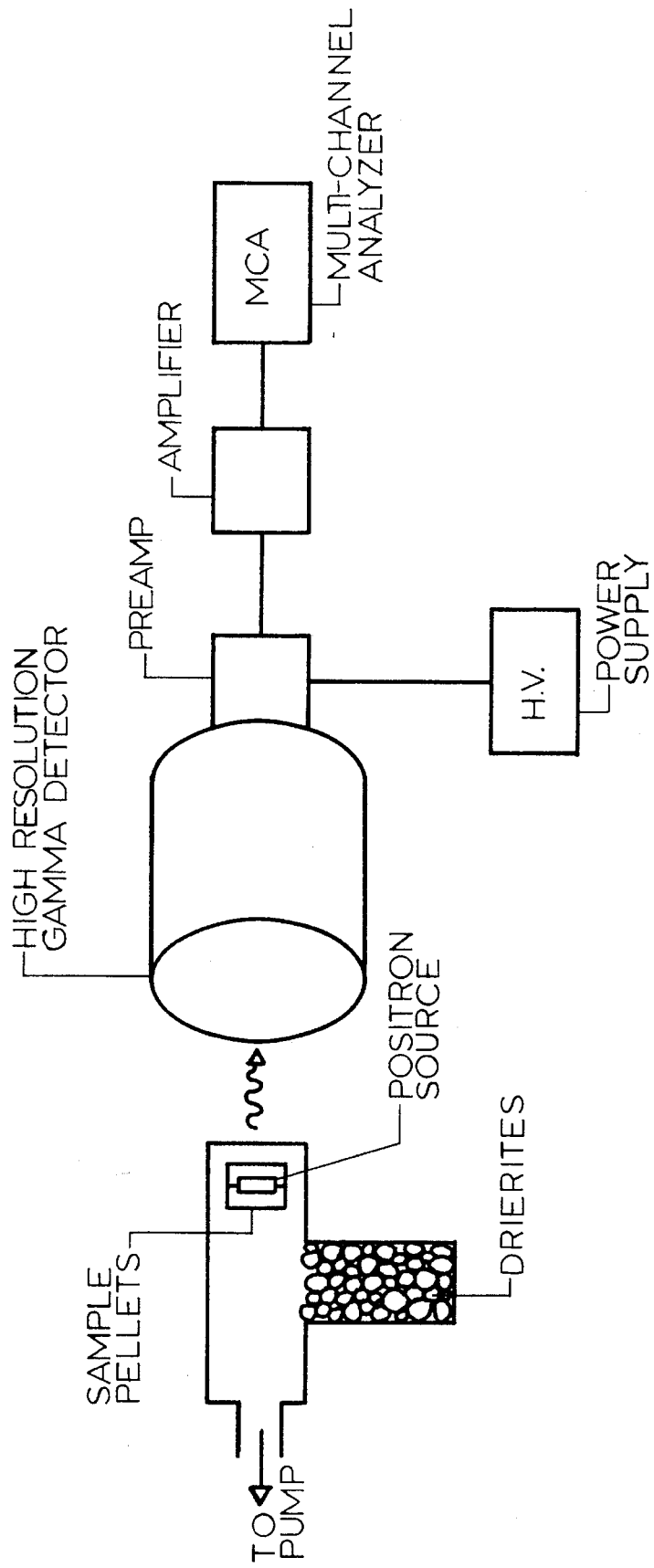
FIG. 1 shows a schematic diagram of an arrangement using a high resolution gamma detector and a sandwiched sample holder.

The energy distribution curve of the annihilation radiation is monitored by a high resolution gamma detector, e.g., the planar high purity germanium gamma detectors (see FIG. 1). Signals from the gamma detector are fed into a stable spectroscopic amplifier (e.g., ORTEC model 572) whose output is sent to a multi-channel analyzer with a 8192 channel ADC(Amplitude-Digit Converter) for spectrum analysis and data storage.

Positron source used for the measurements is usually the radioisotope Na-22 with an activity of 5–10 micro Curie which is enveloped in a thin mylar or metal (e.g., gold) sheet. The source is then sandwiched between two sample pellets. Each pellet is made by pressing about 0.2 g of the sample powder under a load of about 2500 lbs into a circular disk of 12.5 mm in diameter and 2 mm in thickness. The source-sample assembly is placed in a plastic cylinder which is connected to a vacuum pump.

This process, unlike most other surface measurement techniques, is extremely efficient. It normally takes only about twenty minutes to acquire a statistically satisfactory spectrum. The lineshape parameter S is determined by taking the central area within 20 channels in the middle and total area within 200 channels. Unlike the positron lifetime spectrum analysis, this method is independent of data-treatment procedures. Strong evidences have been found to support this method which are herein demonstrated by the following examples.

3. The Two-Dimensional Momentum Distribution Method

Figure 3:
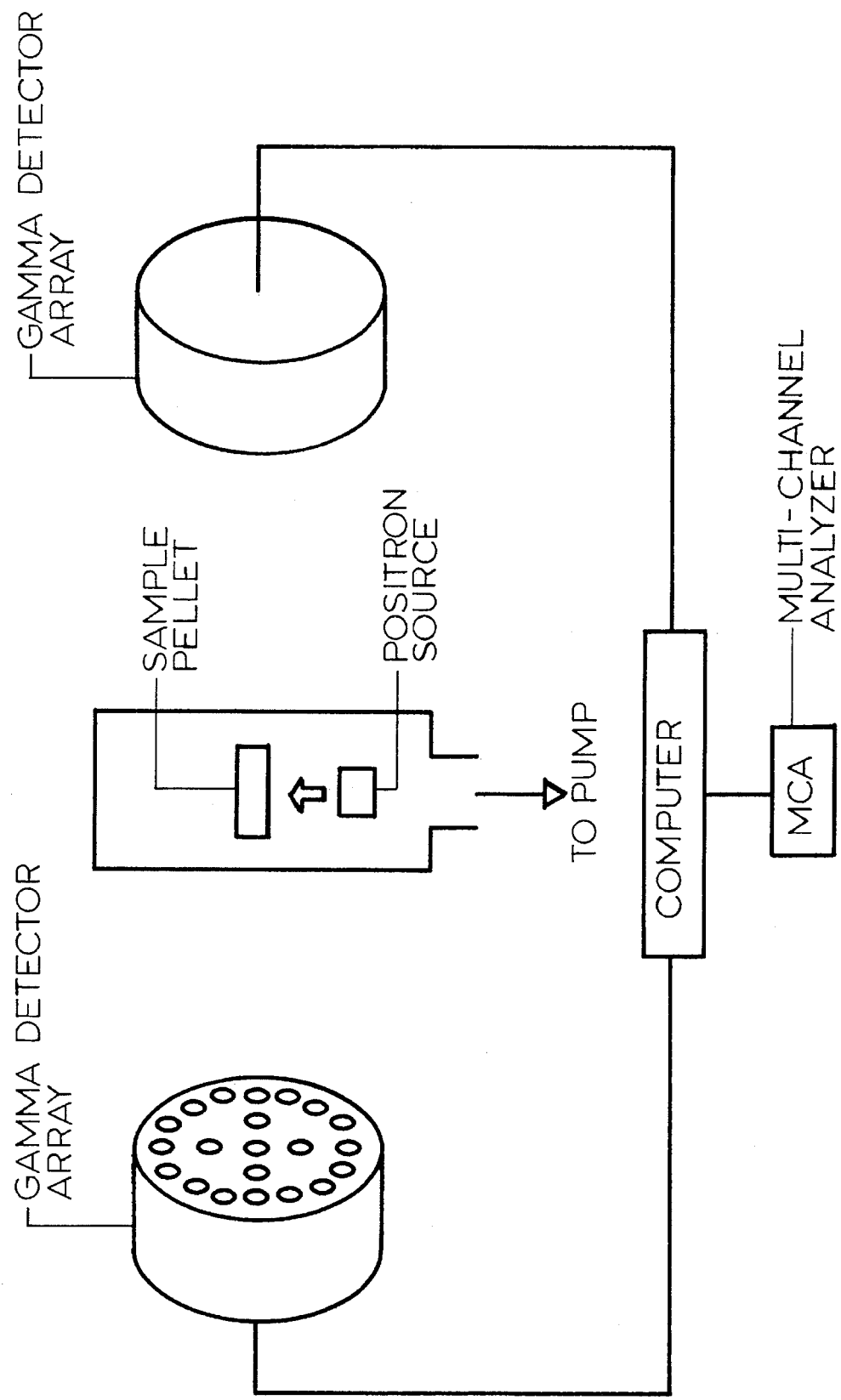
FIG. 3 is a simplified diagram showing the arrangement for the two-dimensional angular correlation measurements.
Figure 4:
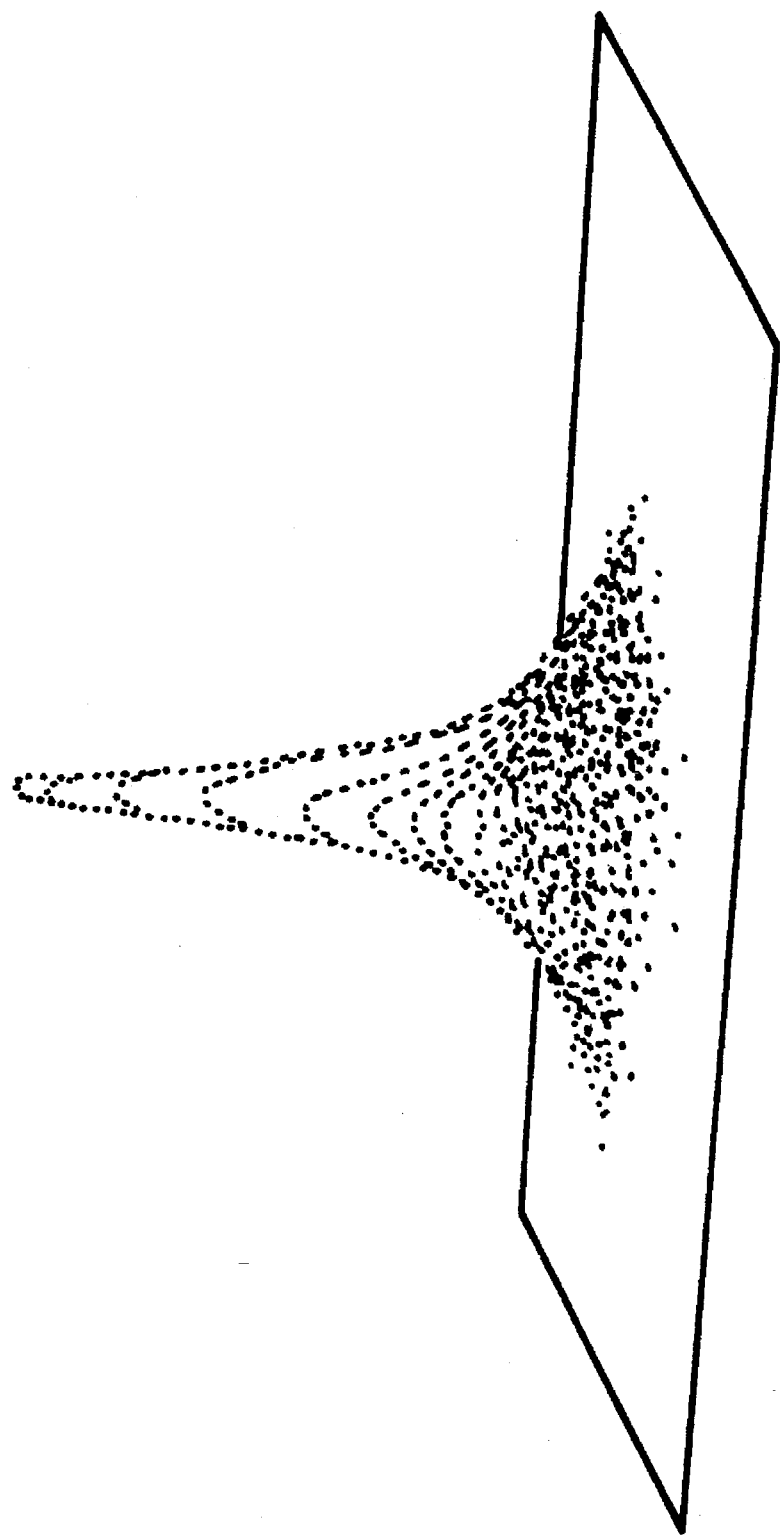
FIG. 4 shows a typical two-dimensional spectrum obtained by using the set-ups shown in FIG. 3. The sharp central peak of the spectrum is attributed to positronium annihilations.
Figure 5:
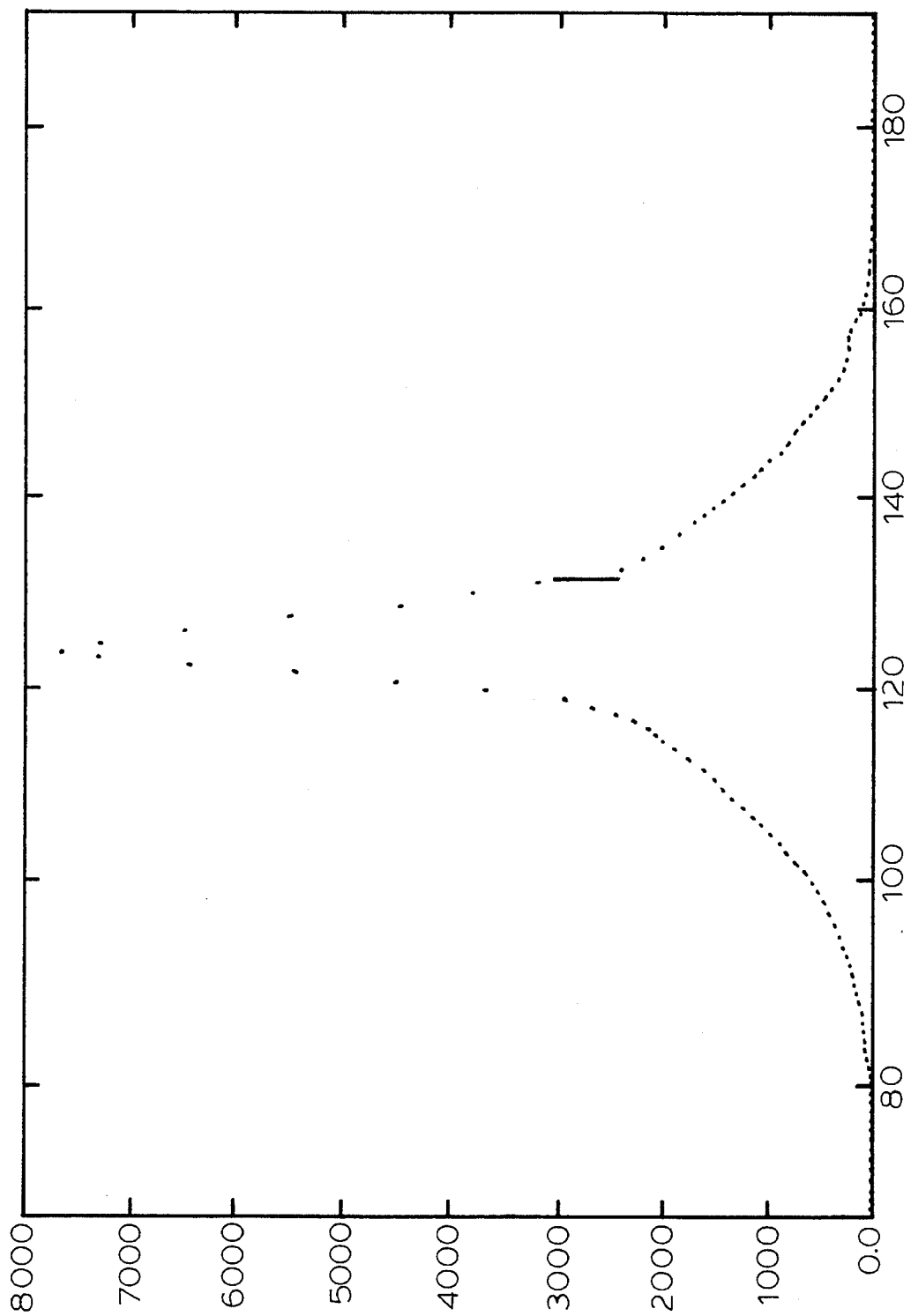
FIG. 5 is a vertical cross section through the peak of the spectrum as shown in FIG. 4. These type of graphs are used for the calculation of lineshape parameters.

In another aspect, this invention comprises another embodiment of an alternative method for the surface characterization by the lineshape parameter measurements using the two-dimensional angular correlation of the annihilation gamma rays. The principle of positron annihilation in catalytic materials is the same as afore-described. FIG. 3 presents a schematic diagram of the experimental set-ups. Angular distribution of the gamma rays in solids corresponds to the electron momentum distribution of the sample, which also exhibits a broad gaussian-like shape. Gammas from positronium annihilation is represented by a sharp narrow peak sitting on top of the gaussian distribution (see FIG. 4). The two-dimensional measurement has a much better counting efficiency than the one-dimensional method. With a positron source(Na-22) of about 20 milliCurie, a good spectrum would need only about ½ hours. It also has an improved angular resolution which enables one to identify the positronium peak by visual inspection. FIG. 5 is a graph by taking a slice through the center of the two-dimensional distribution (FIG. 4) which provides a basis for evaluating the lineshape parameter S. This invention pertains to the discovery for the first time excellent correlations between lineshape parameter S and protonic acidity of catalyst's surface. The present invention is illustrated by the following examples.

EXAMPLE 1

Powder samples of gamma-alumina were calcined at various temperatures to produce samples with different surface areas. The surface area of each sample was determined by measuring the amount of nitrogen absorbed at liquid nitrogen temperature on the solid surface using a Monasorb Surface Area Analyzer by Quantachrom Corp.. The results are contained in Table I.

TABLE I

| Sample No. | Temperature(°C.) (1 hr.) | Area(m²/g) |
| --- | --- | --- |
| 1 | 500 | 224 |
| 2 | 600 | 212 |
| 3 | 700 | 190 |
| 4 | 800 | 175 |
| 5 | 900 | 164 |
| 6 | 1000 | 123 |
| 7 | 1100 | 78 |

The powder sample of each specific surface area was pressed into a pellet of 12.5 mm in diameter and about 2 mm thickness at a 2500 lbs. weight load. Each pellet had a mass of about 0.2 g. A positron source of radioisotope Na-22 with an activity of about 5 microCurie was enveloped in ¼ mil thick mylar film, which was then sandwiched between two sample pellets with the same surface area.

The source-sample assembly was placed in a plastic cylinder which can be evacuated. The annihilation gammas were measured by a high resolution planar high purity germanium detector (Princeton Gamma-Tech Model NSP1513 was used). Signals from the detector were fed into a spectroscopy amplifier (Canberra Model 2021 was used) and the output of the amplifier was connected to a multi-channel analyzer with a 8192 channel ADC (Nucleus Model PCA II was used). FIG. 1 shows the physical arrangement in a schematic diagram. The measurements were performed at room temperature. The distance between the sample and the detector was about 5 cm.

Figure 2:
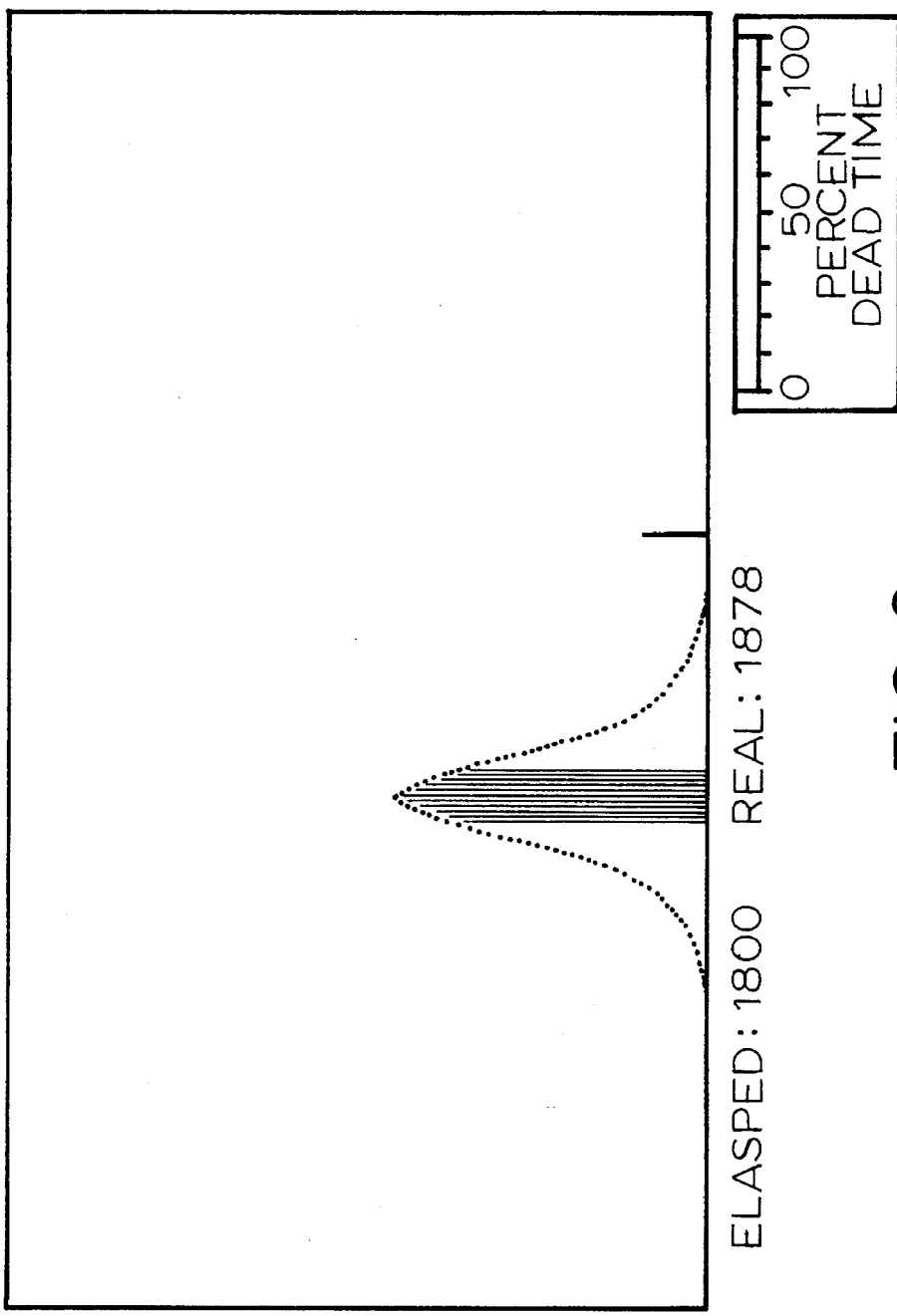
FIG. 2 is a typical gamma spectrum obtained by using the arrangement shown in FIG. 1.

FIG. 2 shows a typical spectrum thus obtained. Lineshape parameter was determined for each sample from a central area in the spectrum which lies within ±10 channels from the peak and a total area within ±100 channels from the peak.

Figure 6:
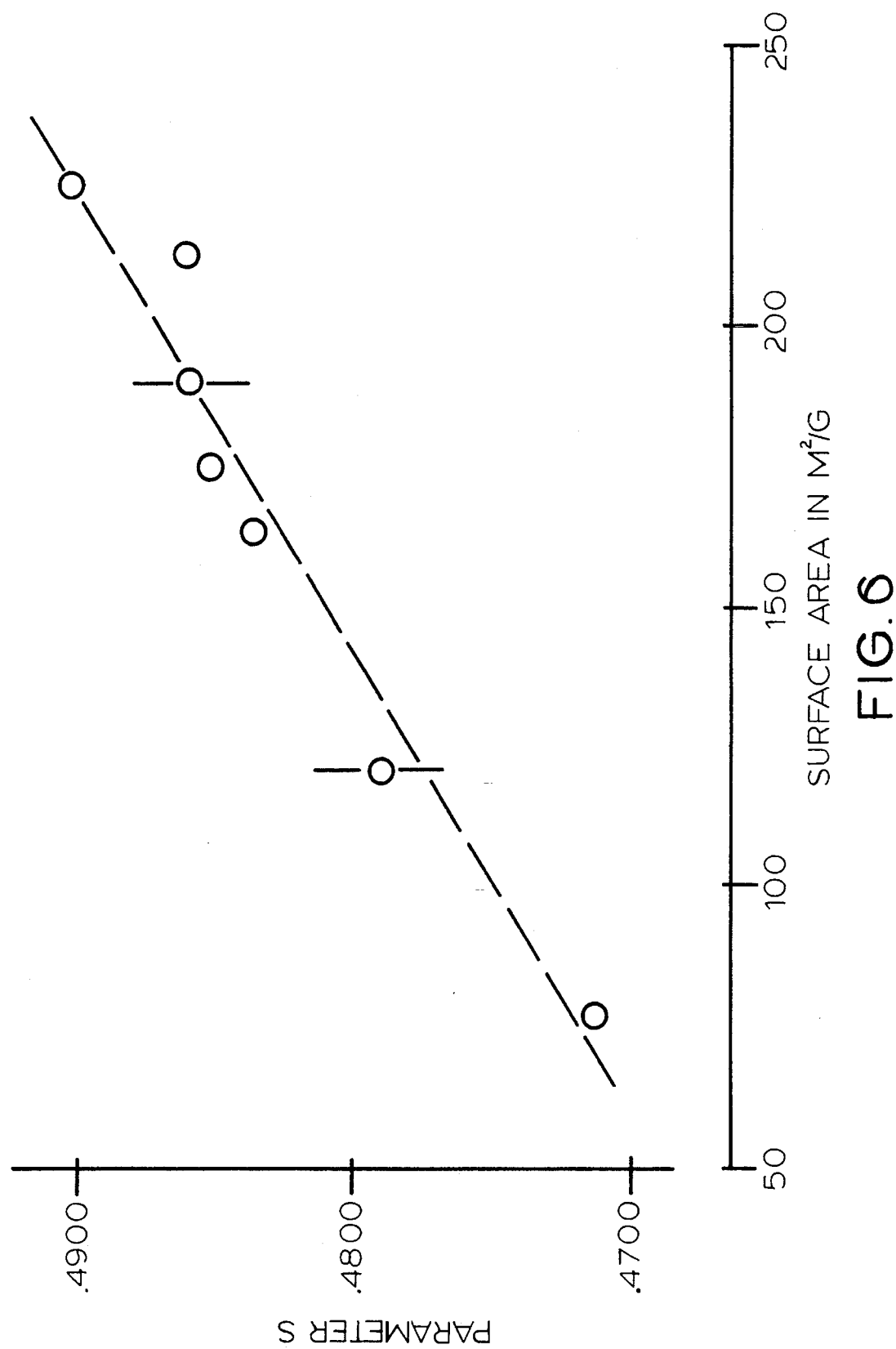
FIG. 6 shows the plot of lineshape parameter S vs the surface area in gamma-alumina.

FIG. 6 is a plot of lineshape parameter S versus sample surface area. The correlation between the parameter S and surface area is evident. It demonstrates for the first time that lineshape of the annihilation gamma spectrum is an effective parameter to monitor any changes in surface areas of the porous materials.

EXAMPLE 2

Figure 7:
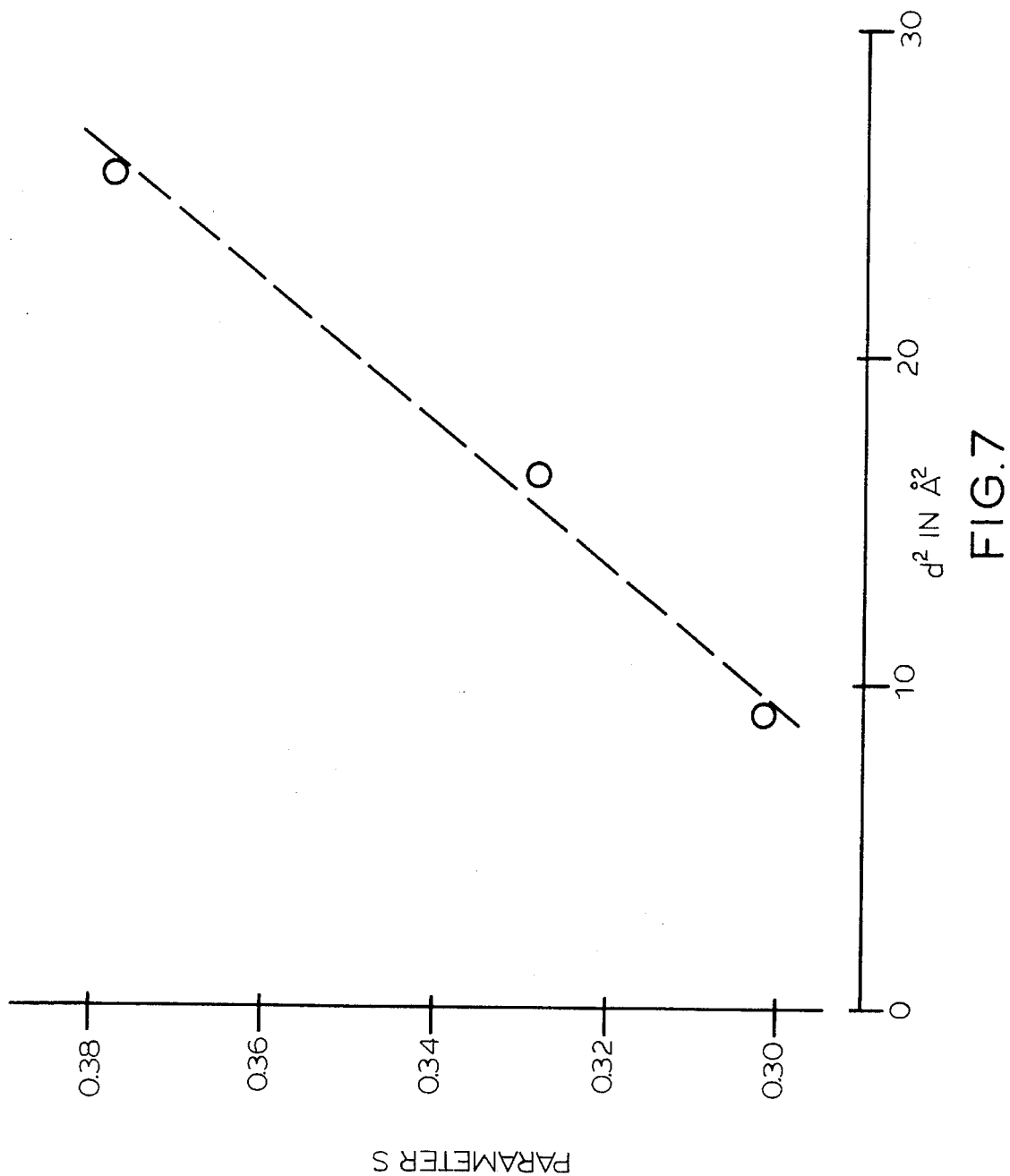
FIG. 7 shows the plot of lineshape parameter S vs diameter squared for Y zeolites with aperture diameters of 3 Å, 4 Å, and 5 Å.

In this example, all measurement techniques and preparation of sample pellets are the same as those used in Example 1. The samples are Y zeolites with aperture diameters of 3 Å, 4 Å, and 5 Å. The results of the measurements in this example are shown in FIG. 7 which is a plot of lineshape parameter S vs diameter squared. Again, it demonstrated the proportionality of parameter S and the surface area.

EXAMPLE 3

Figure 8:
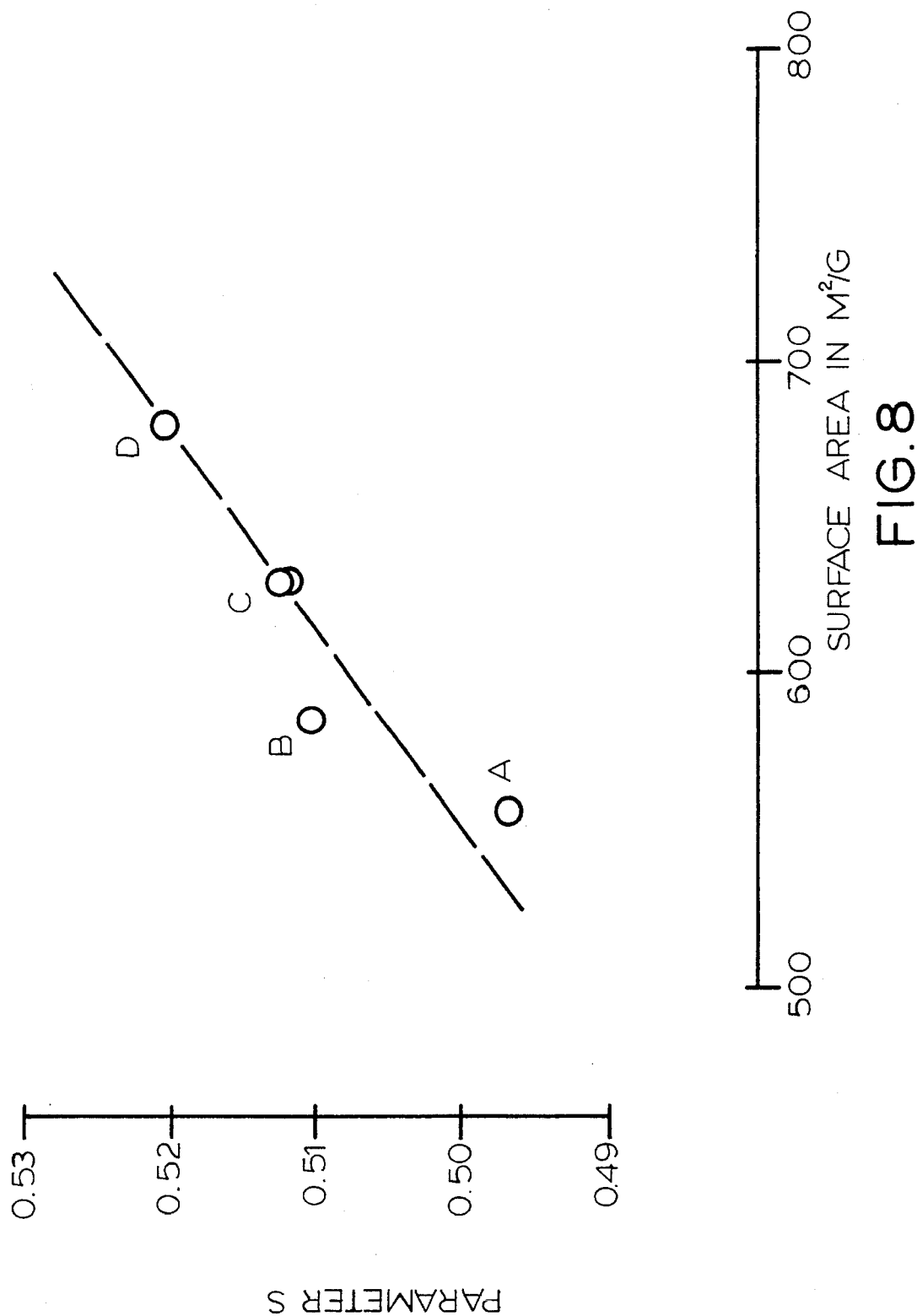
FIG. 8 shows the plot of lineshape parameter S vs surface areas of samples, A: ZSM-5(a), B: NaY(a), C: ZSM-5(b), and D: NaY(b).

All experimental conditions are the same as Example 1. In this example, the samples being measured were different types of zeolites with different surface areas. The plot of lineshape parameter S vs surface area is shown in FIG. 8; it evidenced the correlation between the positron annihilation lineshape parameter S and the sample's surface area even when the samples used are of different types of materials.

EXAMPLE 4

In this example, the two-dimensional angular correlation apparatus was used. Its experimental arrangement is shown in FIG. 3. Polyenergetic positrons from a Na-22 source impinge upon a sample pellet made in the same way as in Example 1. FIG. 4 shows a three dimensional display of the result with the sharp, narrow positronium peak clearly visible at the center. The sample material for this example was the ammonium-form ZSM-5 zeolite. The sample has been examined by the thermogravimetric analysis from 25° C. to 800° C. The decomposition and desorption of ammonia from the sample was found to start at about 300° C. Since the release of each ammonia molecule leaves a proton behind, when the ammonia concentration in the sample is reduced, the protonic acidity of the sample will increase correspondingly as a result of the decomposition,

$NH_4^+—ZSM5—NH_3+H^+—ZSM5.$

Protons can reduce the positronium population through oxidation. Therefore, the samples having been heated to temperatures above 300° C. contain less ammonia, hence, have smaller lineshape parameter S values.

Figure 9:
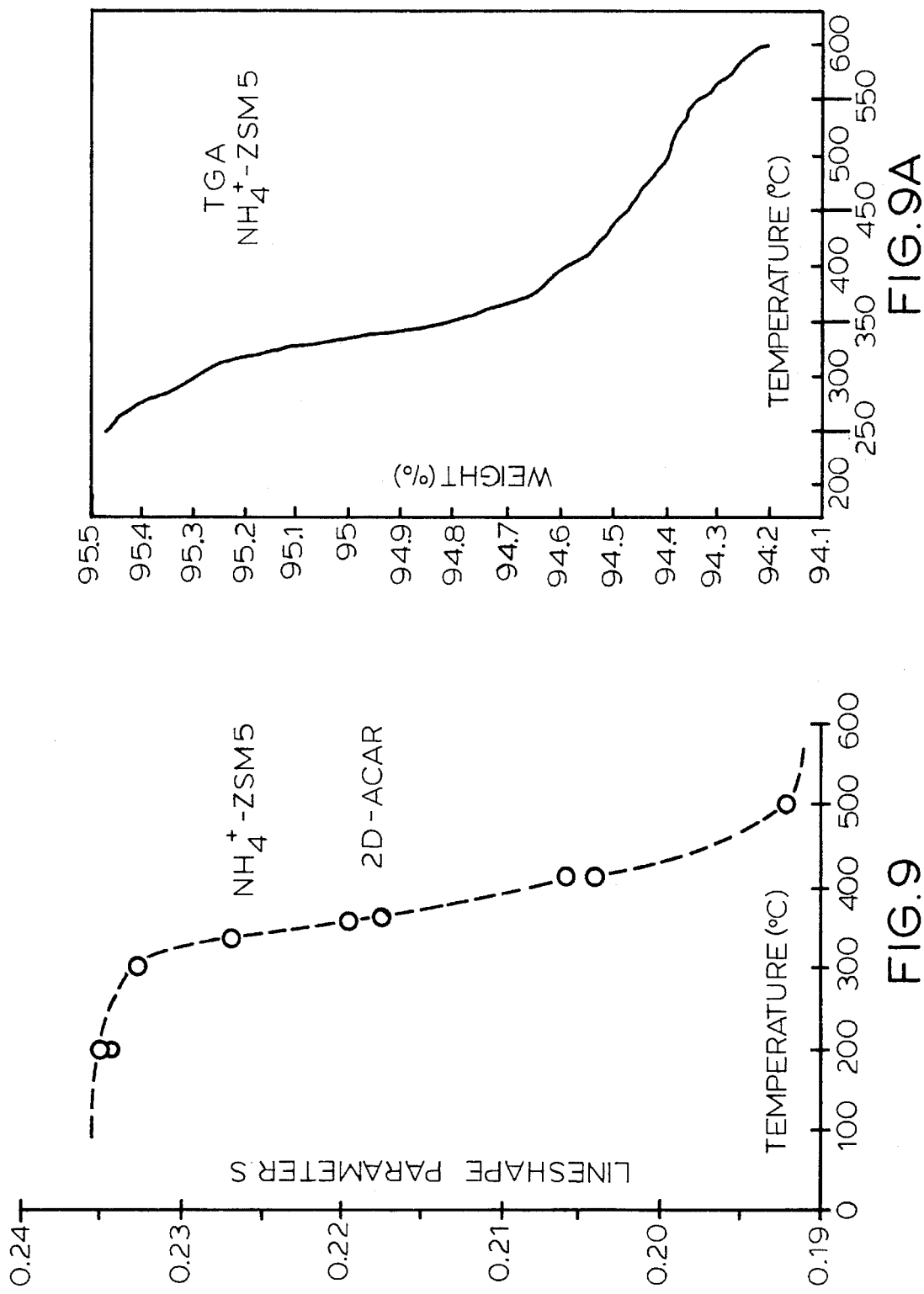
FIGS. 9A shows the plot of lineshape parameter S determined by using two-dimensional angular correlation method for the ammonium form ZSM-5 samples vs the sample pretreatment temperature. The curve from thermogravimetric measurement is also included for comparison as FIG. 9A.

FIGS. 9 and 9A respectively show the plot of lineshape parameter S and TGA vs temperature. The effectiveness of monitoring the change in acidity of a sample by lineshape of the positron annihilation radiation is evident. The two-dimensional angular correlation measurement is also a time-efficient method. With a positron source of Na-22 with an activity of about 30 milliCurie, for example, a good spectrum of two-dimensional measurement would take only about 20 minutes.

EXAMPLE 5

Figure 10:
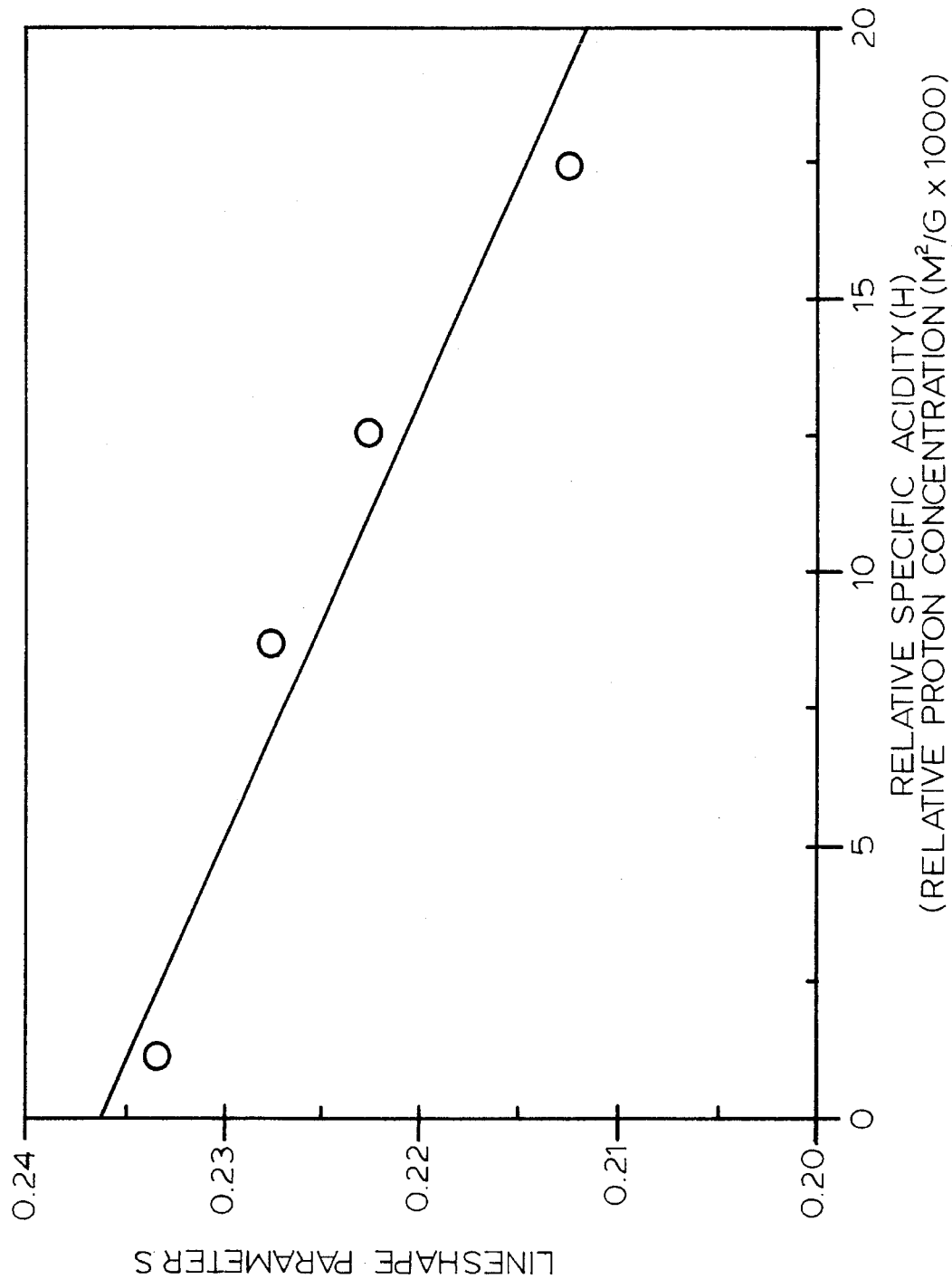
FIG. 10 shows the plot of lineshape parameter S determined by using the two-dimensional angular correlation method vs the relative specific acidity (acidity per unit surface area) for $NH_4$-ZSM5 samples.

Lineshape parameter S for catalytic materials is a function of both surface area and protonic acidity as demonstrated in the above examples. It should be, therefore, a single function of specific acidity (acidity per unit surface area) denoted by H. FIG. 10 displays a plot of lineshape parameter S vs. relative specific acidity for samples $NH_4$—ZSM5. The lineshape parameter S's in this example were measured by using the two-dimensional angular correlation as illustrated in Example 4, and the relative acidity values were determined from the TGA ammonia desorption curve. The surface areas of the samples used in this example were measured by the conventional nitrogen adsorption method. Excellent linearity between the lineshape parameter S and the relative specific acidity (H) is displayed in FIG. 10.

Although the invention has been illustrated by the preceding examples, it is not to be construed as being limited thereby; but rather, the invention encompasses the generic area as hereinbefore disclosed. Various modifications and embodiments can be made without departing from the spirit and scope thereof.

PUBLICATIONS CITED

1. J. Lahtinen and A. Vehanen, "Application of Positron Techniques to Surface Studies and Catalysis", Catalysis Letters, Vol 8, 1991, pp. 67–100.
2. Y. Ito and T. Takano, "Positron Annihilation in Synthetic Zeolites", Applied Physics A, Vol. 45, 1988, pp. 193–201.
3. K. Venkateswaran, K. L. Chen, and Y. C. Jean, "Application of Positron Annihilation to Study the Surface Properties of Porous Resins", Journal of Physical Chemistry, Vol. 88, 1984, pp. 2465–2469.
4. M. B. Perkal and W. B. Walters, "Positron Annihilation in Synthetic Zeolites 4A and 13X", Journal of Chemical Physics, Vol.53, 1970, pp. 190–198.
5. H. Nakanishi and Y. Ujihira, "Application of Positron Annihilation to the Characterization of Zeolites", Journal of Physical Chemistry, Vol. 86, 1982, pp. 4446–4450.
6. W. F. Huang, R. Ochoa, and R. Miranda, "Positronium-Bronsted Acid Site Interaction in a Silica-Alumina Catalyst", Physics Letter A, Vol. 158, 1992, pp. 417–
7. D. Farcasiu, G. Miller, A. Ghenciu, and H. S. Cao, "A New Method of Determining the Acidity of Liquid and Composite Acid Catalysts", 13th North American Meeting of the Catalysis Society, Pittsburgh, Pa., May 2–6, 1993.

I claim:

1. A process for determining relative surface area and relative specific acidity of samples of a catalytically-active material by comparison of positron annihilation lineshapes generated from an annihilation gamma ray spectrum of those samples of the material comprising:

(a) determining the positron annihilation lineshape from a gamma ray spectrum generated from annihilation of positrons in a reference sample of the catalytically-active material;

(b) preparing a second sample of the catalytically-active material for exposure to positrons from a positron source;

(c) exposing the second sample of the catalytically-active material to positrons;

(d) detecting the annihilation gamma ray spectrum by using one or more gamma ray detectors and evaluating the lineshape parameter of the second sample; and (e) comparing the lineshape parameters of positron annihilation of the second sample of catalytically-active material to that of the reference sample to determine the relative specific acidity or surface area of the second sample with respect to the reference sample.

2. The process of claim 1 wherein the source of positrons is a single source directed against the second sample of the catalytically-active material and the reference sample, wherein said catalytically-active material surrounds the source of positrons.

3. The process of claim 1 wherein the second sample of catalytically-active material and the reference sample are exposed to the positrons from only one side of the samples.

* * * * *